(12) United States Patent
Omura et al.

(10) Patent No.: US 6,486,197 B1
(45) Date of Patent: Nov. 26, 2002

(54) SUBSTANCE FT-0554 AND PROCESS FOR PRODUCING THE SAME

(75) Inventors: Satoshi Omura; Kazuro Shiomi; Rokuro Masuma; Yuzuru Iwai, all of Tokyo (JP)

(73) Assignee: The Kitasato Institute, Tokyo (JP)

( * ) Notice: Subject to any disclaimer, the term of this patent is extended or adjusted under 35 U.S.C. 154(b) by 0 days.

(21) Appl. No.: 09/509,770

(22) PCT Filed: Sep. 17, 1998

(86) PCT No.: PCT/JP98/04178

§ 371 (c)(1),
(2), (4) Date: Aug. 3, 2000

(87) PCT Pub. No.: WO99/24439

PCT Pub. Date: May 20, 1999

(30) Foreign Application Priority Data

Nov. 11, 1997 (JP) .............................................. 9-308222

(51) Int. Cl.$^7$ .............................................. A61K 31/35
(52) U.S. Cl. ....................................... 514/456; 549/285
(58) Field of Search ........................... 514/456; 549/285

(56) References Cited

FOREIGN PATENT DOCUMENTS

WO          97/32868          9/1997

OTHER PUBLICATIONS

CRC Handbook of Antibiotics, pp. 73–81, 1984.*
R.K. Bhatt et al., "A New Clerodane Derivatives From Tinospora Cardifolia," Phytochemistry, vol. 27, No. 4, pp. 1212–1216, 1988, XP000999227.

Boris Schilling et al., "Amine Oxidases from Aspergillus Niger: Identification of a Novel Flavin–Dependent Enzyme", Biochimica et Biophysica Acta, vol. 1243 (1995) pp. 529–537.

Yoshiharu Inoue et al., "Metabolism of 2–oxoaldehyde in Mold Purification and Characterization of Two Methyl–g-lyoxal Reducatases from Aspergillus Niger", Eur. J. Biochem, vol. 171 (1988) pp. 213–218.

* cited by examiner

Primary Examiner—Amelia Owens
(74) Attorney, Agent, or Firm—Young & Thompson

(57) ABSTRACT

The present invention is to obtain novel FT-0554 substance which is useful for treatment of helminthiasis. The present invention comprising the steps of culturing the microorganism belonging to fungi having producing activity of FT-0554 substance represented by the following formula [I]

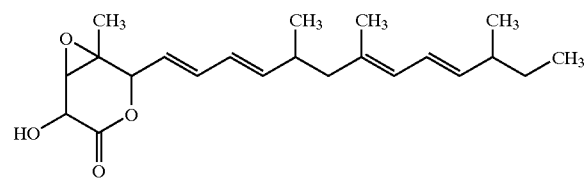

subjected ho accumulation of FT-0554 substance in the cultured medium, and isolating FT-0554 substance from the said cultured mass. The medicament useful for treatment of parasitic infection, specifically helminthiasis can be obtained.

2 Claims, 2 Drawing Sheets

SUBSTANCE FT-0554 AND PROCESS FOR PRODUCING THE SAME

FIELD OF THE INVENTION

This invention relates to novel FT-0554 substance useful for treatment for infection of parasite, especially helminth, and its production.

PRIOR ARTS

Parasitosis is reducing as a result of improvement in sanitary conditions and progress of anthelmintics. Recently, however, the import parasitosis, zoonotic parasitosis, opportunistic parasitosis and parasitosis originated from perishable foods are prevailing and become crucial problems. Further the parasitosis produces large economical burdens in the stock-farming and agriculture. For infection of helminth in the parasite, at present, avermectins, mebendazole, praziquantel, and others are used for treatment of helminth.

PROBLEMS TO BE SOLVED BY THE INVENTION

Anthelmintics used at present, such as avermectins, mebendazole and praziqbantel, are not always sufficient for satisfactory in usefulness and toxicity, and the anthelmintics, which can solve these problems, are strongly, required.

Consequently, the present invention provides novel FT-0554 substance, which can satisfy the above requirements, and its production.

MEANS FOR SOLVING THE PROBLEMS

We have studided NADH-fumarate reductase, which was one of the promising targets against anthelmintics, in the electron transport system of the helminth, and explored for screening in the microbial culture. We have found that novel FT-0554 substance had NADH-fumarate reductase inhibitory activity, and completed the present invention according to this acknowledge.

An object of the present invention is to provide FT-0554 substance shown by the compound of the formula [I]

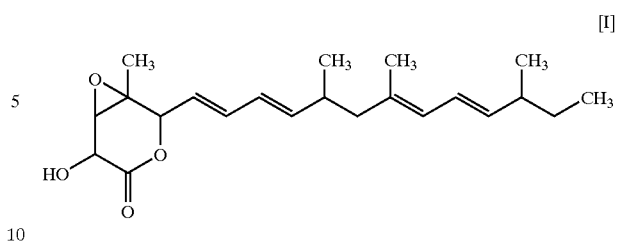

Another object of the present invention is to provide a process for production of FT-0554 substance of formula [I]

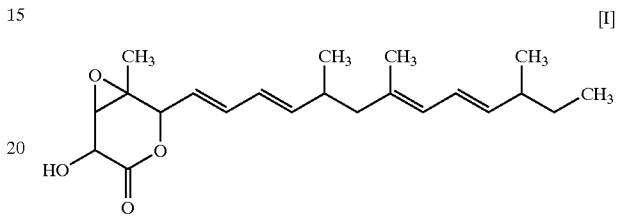

which comprises culturing a microorganism belonging to fungus having FT-0554 substance producing activity, accumulating FT-0554 substance in the cultured medium and isolating FT-0554 substance from the cultured medium.

Further object of the present invention is to provide a microorganism belonging to fungi and having FT-0554 substance producing activity of the above process being *Aspergillus niger* FT-0554. Still further object of the present invention is to provide a microorganism belonging to fungi and having FT-0554 substance producing activity being *Aspergillus niger* FT-0554.

FT-0554 substance producing microorganism is the fungi having FT-0554 substance producing activity and is not limited. Preferable example of a microorganism used for production of FT-0554 is a fungus strain FT-0554 isolated from a newly collected sponge by the inventors of the present invention.

Taxonomical properties of the microorganism are illustrated as follows.

Taxonomical properties of a strain FT-0554.

(1) Cultured Properties on Various Media

Results of macroscopic observation of the strain of the present microorganism cultured at 25° C. for 7 days are shown in Table 1.

TABLE 1

| Medium | Growth condition on the medium (diameter of colony) | Color of surface of colony | Color of reverse side of colony | soluble pigment |
|---|---|---|---|---|
| Czapek-yeast extract agar | good (82 mm) velvety, entire | black brown | pale yellow | none |
| Malt extract agar medium | good (81 mm) velvety, entire | black brown | pale yellow | none |
| 20% sucrose Czapek-yeast extract agar medium | good (82 mm) velvety, entire | black brown | pale yellow | none |
| Potate-glucose agar medium | good (>85 mm) velvety, entire | black brown | pale yellow | none |
| Miura agar medium | moderate (40 mm) velvety, entire | black brown | white | none |

(2) Morphological Properties

The microorganism of the present invention shows good growth on Czapek-yeast extract agar medium which contains seawater 50% (salt content 3.4%), malt extract agar medium, Czapek-yeast extract agar medium which contains sucrose 20% and potato-glucose agar medium, with abundance of conidia.

Microscopical observation of colonies grown on Czapek-yeast extract agar medium shows transparent hyphae with septa, straight grown conidiophore on the substrate mycelia with length 500 $\mu$m–2.5 mm, and foot-cell in the basement. Tops of conidiophores are hypertrophic from spherical to subspherical with forming vesicles of diameter 35–60 $\mu$m.

Plural aspergillae consist of metulae and phialides with the size of 8.4–11.4×2.4–3.4 $\mu$m and 5.4–8.6×2.8–3.3 $\mu$m, respectively. Whole of the vesicles is covered with metulae with forming conidial heads segmented from spherical to cylindrical. Conidia is globose with a size of diameter 3–4.5 $\mu$m having smooth to rough surface.

(3) Physiological Properties

1) Optimum Growth Condition

Optimum growth condition of the present strain is pH 5–7, temperature 16–36°C. and seawater concentration $^{1)}$ 50–100%. $^{1)}$: salt concentration 3.4% natural seawater is used 2) Growth Condition Growth range of the strain is pH 3–10, temperature 12–45° C. and seawater concentration $^{2)}$ 0–100%. $^{1}$: salt concentration 3.4% natural seawater is used 3) Nature Aerobic As shown in the above, culture condition, taxonomical properties and physiological properties of the present microorganism strain FT-0554 are compared with the known microorganism strains. The present strain is identified as belonging to Aspergillus niger and referred to *Aspergillus niger* FT-0554.

The present microorganism strain has deposited as *Aspergillus niger* FT-0554 FERM P-16399 in National Institute of Bioscience and Human-Technology, Agency of Industrial Science and Technology, Ministry of International Science and Technology, 1–3, Higashi 1—chome, Tsukuba-shi, Ibaraki-ken, Japan on Sep. 1, 1997. Further, the present microorganism strain was transferred to the microorganism deposition under Budapest Treaty in National Institute of Bioscience and Human-Technology, Agency of Industrial Science and Technology, Ministry of International Science and Technology, 1–3, Higashi 1-chome, Tsukuba-shi, Ibaraki-ken, Japan on Jul. 31, 1998, and was given deposition No. FERM BP-6443 from the International Deposition Authority.

Production of FT-0554 substance of the present invention can be performed by culturing microorganism belonging to fungi having producing activity of FT-0554 substance and isolating from the cultured mass and purifying the product. The microorganism strain used in the present invention can be the above microorganism strain, its variants and mutants, and all strains having FT-0554 substance producing activity belonging to fungi.

Nutritional sources for production of the above FT-0554 substance can be a nutritional source for fungi. Examples of nitrogen sources are commercially available peptone, meat extract, corn steep liquor, cottonseed powder, peanut powder, soybean flour, yeast extract, NZ-amine, casein hydrolyzate, sodium nitrate, ammonium nitrate and ammonium sulfate. Example of carbon sources are carbohydrate such as glycerin, starch, glucose, galactose and mannose, or carbon source such as fats and oil, and inorganic salts such as sodium chloride, phosphate, calcium carbonate and magnesium sulfate. These can be used with or combination thereof.

Trace metallic salt and animal, vegetable or mineral oil as anti-form agent can be added if necessary. These are substance, which can be assimilated by the producing strain and are useful for production of FT-0554 substance, can be used. All the known medium for culturing the fungus can be used. Mass production of FT-0554 substance can preferably be performed by a liquid culture. Culturing temperature can be applied within the range of growing the producing microorganism strain and producing FT-0554 substance. Culturing can be performed by selecting suitable conditions depending on the nature of FT-0554 substance producing strain.

FT-0554 substance can be extracted by water immiscible organic solvent such as chloroform and ethyl acetate from the culture liquid. In addition to the above extraction method, known isolation method used for lipophilic substance, for example adsorption chromatography, gel filtration chromatography, scratching from thin layer chromatography, centrifugal counter current chromatography, HPLC, and the like with or without combination thereof or repeated operation, can be applied to obtain purified substance.

Physico-chemical properties of FT-0554 substance of the present invention are shown as follows.

(1) Nature: white powder or amorphous
(2) Molecular weight: 361.2374 (M+H, high resolution fast atom bombardment mass spectroscopy)
(3) Molecular formula $C_{22}H_{32}O_4$
(4) Specific rotation: $[\alpha]_D^{25}$=+35.3° (c=0.1, 1-propanol)
(5) UV absorption maximum (in 1-propanol): As shown in FIG. 1, maximum absorption at 205 nm (shoulder, $\epsilon$=10800) and 231 nm ($\epsilon$=21000).
(6) IR absorption maximum (KBr Tab): As shown in FIG. 2, maximum absorption at 3430, 2960, 2920, 2850, 1740, 1660, 1460, 1400, 1380, 1180, 1120 and 1000 cm $^{-1}$
(7) $^1$H-NMR: chemical shift in deuterochloroform (ppm) and spin-spin coupling constant (Hz) in Table 2
(8) $^{13}$C NMR: chemical shift in deuterochloroform (ppm) in Table 2

Solubility in solvent : soluble in chloroform, ethanol, 1-propanol, toluene and ethyl acetate, insoluble in water and n-hexane

(10) Color reaction positive for sulfuric acid and iodine.

Table 2

TABLE 2

| $^{13}$C | $^1$H |
|---|---|
| 170.6 s | |
| 145.2 d | 5.79 dd (1 H, J = 6.9, 15.2) |
| 138.9 d | 5.46 dd (1 H, J = 7.6, 15.2) |
| 137.9 d | 6.37 dd (1 H, J = 10.2, 15.2) |
| 133.7 s | |
| 127.0 d | 5.76 d (1 H, J = 10.9 H z) |
| 126.0 d | 6.02 dd (1 H, J = 10.2, 15.2) |
| 124.6 d | 6.17 dd (1 H, J = 10.9, 15.2) |
| 122.0 d | 5.48 dd (1 H, J = 7.9, 15.2) |
| 80.2 d | 4.92 d (1 H, J = 7.9) |
| 68.0 d | 4.57 s (1 H) |
| 58.5 d | 3.52 s (1 H) |
| 58.2 s | |
| 47.2 t | 1.96 dd (1 H, J = 7.7, 13.7) |
| | 2.09 dd (1 H, J = 7.1, 13.7) |
| 38.6 d | 2.06 m (1 H) |
| 34.8 d | 2.42 m (1 H) |

TABLE 2-continued

| $^{13}C$ | $^1H$ |
|---|---|
| 29.8 t | 1.31 dq (2 H, J = 7.1, 7.3) |
| 20.2 q | 0.98 d (3 H, J = 6.8) |
| 19.4 q | 0.97 d (3 H, J = 6.8) |
| 17.8 q | 1.45 s (3 H) |
| 16.5 q | 1.69 s (3 H) |
| 11.8 q | 0.85 t (8 H, J = 7.3) |

In Table 2, s: singlet, d: doublet, t: triplet, q: quartet, m: multiplet, H: number of proton, and J: spin-spin coupling constant (Hz).

As a result of detailed examination of physico-chemical properties and spectrum data of FT-0554 substance, FT-0554 substance is determined as the following chemical structure.

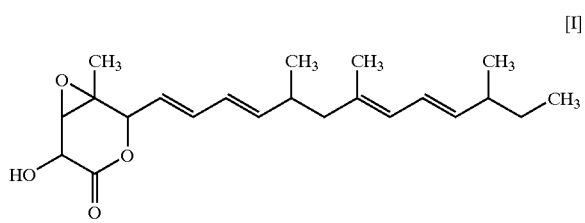

[I]

As shown in the above, physico-chemical properties of FT-0554 substance are explained in detail, however no compound having identical properties have been reported. Consequently, FT-0554 substance is defined as novel substance.

NADH-fumarate reductase inhibitory activity of FT-0554 of the present invention is explained as follows.

Muscles of Ascaris suum were homogenized in 120 mM sodium phosphate solution (pH 7.0) and centrifuged at 3,000×g for 10 minutes to collect the supernatant solution. The supernatant was further centrifuged at 10,000×g for 20 minutes to collect the precipitate. The precipitate was suspended in 120 mM sodium phosphate solution (pH 7.0) to obtain mitochondrial fraction.

After 10 μl of test sample dissolved in 50% dimethyl sulfoxide solution was added into 96 holes microplate, 120 mM sodium phosphate solution (pH 7.0) containing 0.35 mM NADH, 7.2 mM disodium fumarate and 18 mg/ml bovine serum albumin was added thereto, and pre-incubated in the microplate reader ELx808 (Bio-Tek Industries Co.) at 37° C. for 5 minutes.

Mitochondrial fraction of Ascaris suum 10 μl (protein content 0.3 mg) was added therein and incubated at 37° C. for 10 minutes. Absorption of NADH at 340 nm was measured every 15 seconds. As a result of quantitative measurement of NADH-fumarate reductase activity shown by decrease in the slope of absorbancy at 340 nm, 50% inhibition of NADH-fumarate reductase activity were obtained at 2.8 μM of FT-0554 substance. Consequently, FT-0554 substance can be expected to use as drug for treatment or prevention of helminthiasis.

Antimicrobial activity of FT-0554 substance of the present invention is as follows.

Chloroform solution of the compound of the present invention (1 mg/ml) 10 μl is dipped on a filter paper disk (Advantec Co. diameter 6 mm), which is air-dried to remove the solvent. The air-dried to remove the solvent. The dried disks are put on the agar plates containing test organisms, incubated at 37° C. or 27° C. for 24 hours, and diameter of the inhibition zone around the paper disk is measured. Result are shown in Table 3.

TABLE 3

| Test organisms | inhibition zone diameter (min) |
|---|---|
| Escherichia coli KB213 (NIHJ) | – |
| Escherichia coli KB176 (NIRJ JC-2. IFO 12734) | – |
| Pseudomonas aeruginosa P-3 KB105 | + |
| Xanthomonas oryzae KB88 | – |
| Micrococcus luteus KB40 (PCI 1001) | – |
| Staphylococcus aureus KB210 | – |
| Mycobacterium smegmatis KB42 (ATCC 607) | – |
| Bacillus subtilis KB27 (PCI 219) | – |
| Bacteroides fragilis KB169 (ATCC 23745) | – |
| Acholeplasma laidrawii KB174 | – |
| Candida albicans KF1 | 12 |
| Saccharomyces cervisiae KF26 | – |
| Aspergillus niger KF103 (ATCC 6275) | – |
| Pyricularia oryzae KF180 | ± |
| Mucor racemosus KF223 (IFO 4581) | 10 |

As shown in Table 3, FT-0554 substance of the present invention has weak growth inhibitory activity against some microorganisms.

EMBODIMENTS OF THE PRESENT INVENTION

Figure 1:
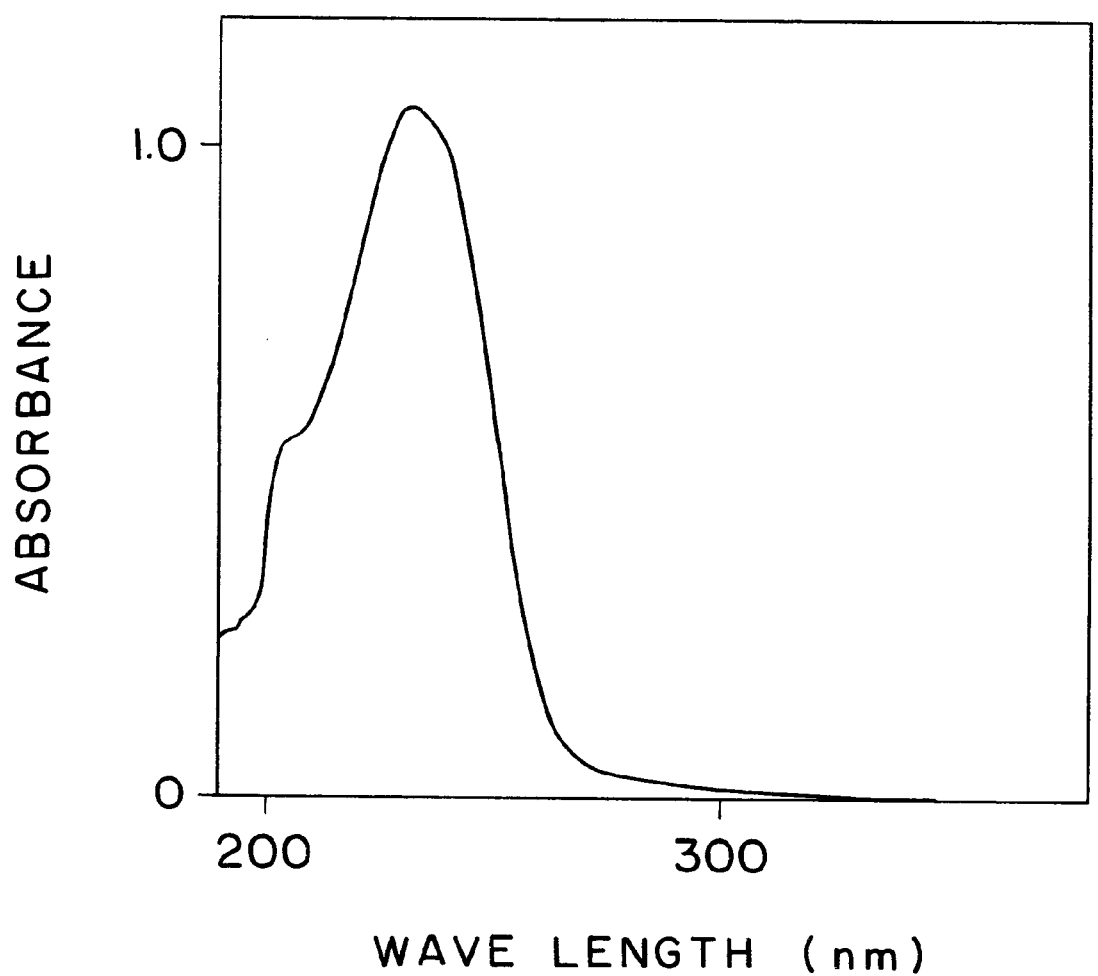
FIG. 1 shows UV spectrum of FT-0554 substance of the present invention in 1-propanol solution (50 μM).
Figure 2:
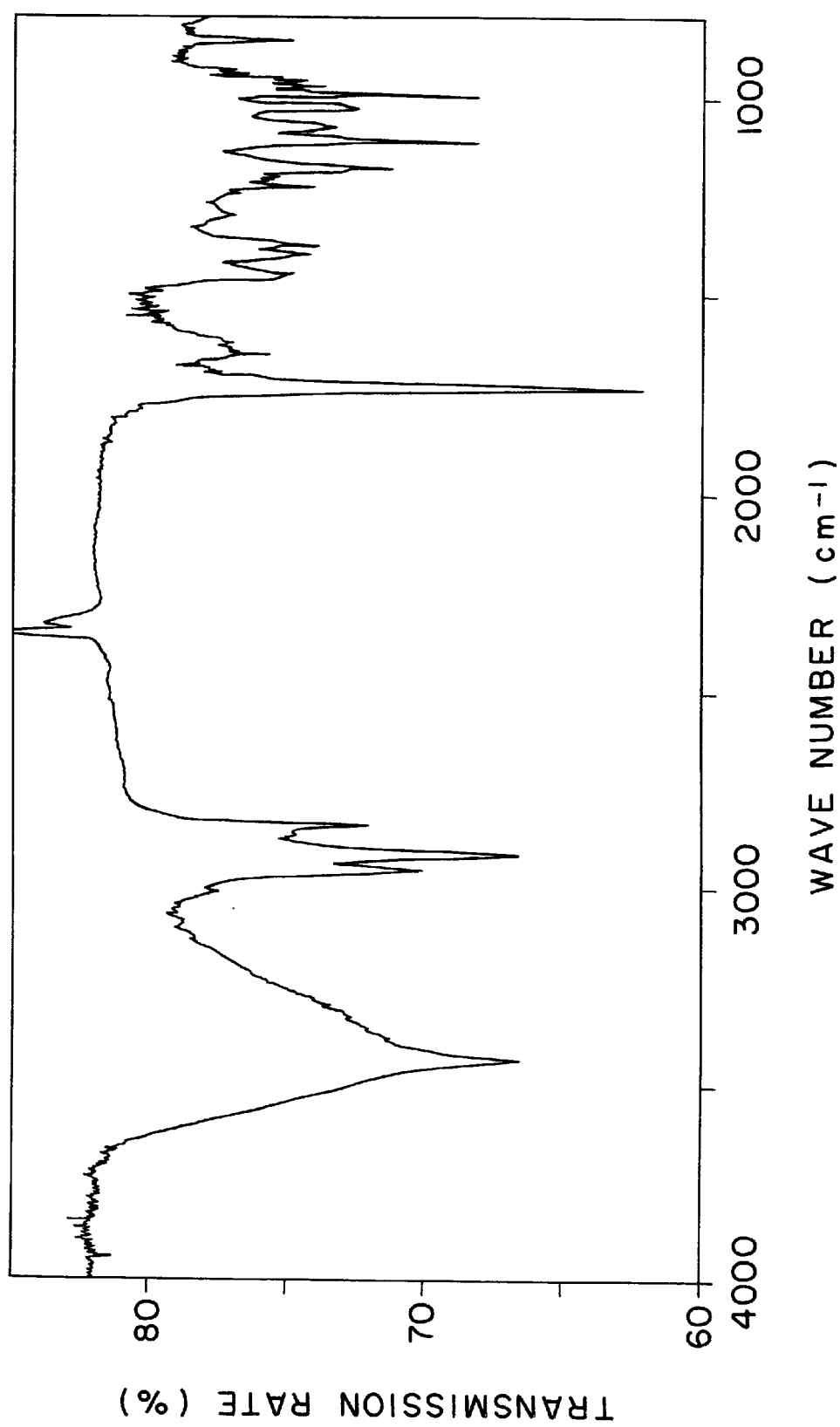
FIG. 2 shows IR spectrum of FT-0554 substance of the present invention (KBr Tab.).

The following examples illustrate the present invention, but is not construed to limit the invention.

EXAMPLE

A loopful of Aspergillus niger FT-0554 (FERM BP-6443) cultured in agar slant medium was inoculated into the liquid medium (pH 7.0) containing glucose 2.0%, polypeptone (Nihon Seiyaku Co.) 0.5%, agar 0.1%, yeast extract (Oriental Yeast Co.) 0.2%, magnesium sulfate 7 hydrate 0.05% and pottassium dihydrogen phosphate 0.1% dissolved in 50% natural seawater (salt concentration 3.4% natural seawater was used) and divided into 100 ml in a 500 ml Erlenmeyer flask, and shake cultured at 27° C. for 2 days.

This seed culture liquid each 1 ml was inoculated into the liquid medium containing potato dextrose broth (Difco Inc.) 2.4% dissolved in 50% natural seawater (salt concentration 3.4% natural seawater was used) divided each 100 ml in a 500 ml Erlenmeyer flask (×30 flasks) and shake cultured at 27° C. for 96 hours.

Cultured liquid medium was centrifuged and obtained inycelia was extracted with ethanol 3 lit. Ethanol was removed in vacuo. Mycelia was again extracted with n-hexane and concentrated in vacuo to obtain crude substance I, 1.9 g. This was charged on the column of silica gel (95 g, Merck Art. 7734) packed with n-hexane, washed with mixture of n-hexane-ethyl acetate (10: 1), and eluated with n-hexane-ethyl acetate (10: 2). The eluate was concentrated in vacuo to obtain crude substance II, 22.7 mg. The crude substance II was charged on a silica gel thin layer plates (Merck Art, 5744) and developed with n-hexane-ethyl acetate (1: 1). Active fraction was scratched and eluated with chloroform-methanol (2: 1). The eluate was concentrated in vacuo to obtain crude substance III, 13.4 mg. Further the substance III was charged on dephadex LH-20 column and eluated with chloroform-methanol (1: 2). The eluate was concentrated in vacuo to obtain FT-0554 substance as white powder 10.0 mg.

EFFECT OF THE INVENTION

As explained hereinabove, FT-0554 substance of the present invention is expected to be a satisfactory and useful medicament for treatment of parasitosis.

What is claimed is:
1. FT-0554 substance of the formula

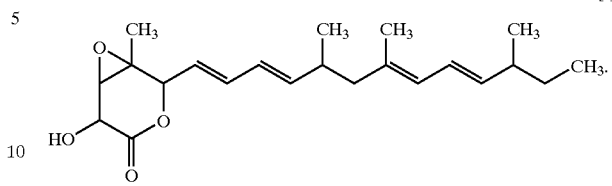

2. NADH-fumarate reductase inhibitor comprising FT-0554 substance.

* * * * *